(12) United States Patent
Shore et al.

(10) Patent No.: US 7,270,805 B1
(45) Date of Patent: Sep. 18, 2007

(54) SKIN LIGHTENING AGENTS, COMPOSITIONS AND METHODS

(75) Inventors: Leonard J. Shore, Oak Ridge, NJ (US); Sheila Alves Rocha, Union City, NJ (US); Martin D. McKinney, Jersey City, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 11/394,012

(22) Filed: Mar. 30, 2006

(51) Int. Cl.
- *A61Q 19/00* (2006.01)
- *A61Q 19/02* (2006.01)
- *A61K 8/00* (2006.01)
- *A61K 8/02* (2006.01)
- *A61K 31/425* (2006.01)

(52) U.S. Cl. .................. 424/62; 424/59; 424/60; 424/400; 424/401; 514/367

(58) Field of Classification Search .............. 424/62, 424/59, 60, 400; 514/367
See application file for complete search history.

(56) References Cited

U.S. PATENT DOCUMENTS

| | | |
|---|---|---|
| 6,132,740 A | 10/2000 | Hu et al. |
| 6,504,037 B2 | 1/2003 | Bradley et al. |
| 6,852,310 B2 | 2/2005 | Harichian et al. |
| 6,861,564 B2 | 3/2005 | Bradley et al. |

FOREIGN PATENT DOCUMENTS

| | | |
|---|---|---|
| JP | 2000-327557 | 11/2000 |
| JP | 2001-010925 | 1/2001 |

OTHER PUBLICATIONS

Ucar, et al., Synthesis and Anticonvulsant Activity of 2(3H)-Benzoxazolone and 2(3H)-Benzothiazolone Derivatives, *J. Med. Chem.*, 41:1138-1145 (1998).

Ucar, et al., "Fries Like" Rearrangement: a Novel and Efficient Method for the Synthesis of 6-Acyl-2(3H)-benzoxazolones and 6-Acyl-2(3H)-benzothiazolones, *Tetrahedron* 54: 1763-1772 (1998).

*Primary Examiner*—Shelley A. Dodson
(74) *Attorney, Agent, or Firm*—Edward A. Squillante, Jr.; Ellen Plotkin

(57) ABSTRACT

Cosmetic compositions and methods, particularly for skin lightening, using N-acylbenzothiazolone compound and derivatives of general formula I as skin lightening agents alone or in combination with other skin benefit agents and together with a cosmetic vehicle:

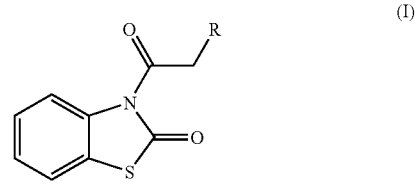

(I)

Where R represents a hydrogen atom, $C_1$-$C_4$ acyl group, or $C_1$-$C_4$ alkyl group. Preferably, the compound is 3-propionylbenzothiazol-2-one, i.e. where R in the formula I is $C_1$ alkyl group.

13 Claims, No Drawings

SKIN LIGHTENING AGENTS, COMPOSITIONS AND METHODS

FIELD OF THE INVENTION

The invention relates to cosmetic compositions and methods using N-acylbenzothiazolones and derivative compounds, and more specifically, using 3-propionylbenzothiazol-2-one and derivative compounds as skin lightening agents.

BACKGROUND OF THE INVENTION

Many people are concerned with the degree of pigmentation of their skin. For example, people with age spots or freckles may wish such pigmented spots to be less pronounced. Others may wish to reduce the skin darkening caused by exposure to sunlight or to lighten their natural skin color. To meet this need, many attempts have been made to develop products that reduce the pigment production in the melanocytes. However, the substances identified thus far tend to have either low efficacy or undesirable side effects, such as, for example, toxicity or skin irritation. Therefore, there is a continuing need for new cosmetic skin lightening agents, with improved overall effectiveness.

For example, certain resorcinol derivatives, particularly 4-substituted resorcinol derivatives, are useful in cosmetic compositions for skin lightening benefits, as disclosed in Hu et al., U.S. Pat. No. 6,132,740; Bradley, et al., U.S. Pat. Nos. 6,504,037 and 6,861,564; Japanese published patent applications JP 2001-010925 and JP2000-327557; and Harichian et al., U.S. Pat. No. 6,852,310.

Applicants have now discovered that N-acylbenzothiazolones, particularly 3-propionylbenzothiazol-2-one, and derivative compounds deliver skin lightening benefits. The general chemical formulas and structures of these compounds are discussed in more detail herein below. The 3-propionylbenzothiazol-2-one and derivative compounds have been found to be cosmetically effective and possibly less irritating to the skin. These compounds of the present invention have not been used in cosmetics, nor have they been used, specifically, for lightening skin.

The synthesis of 3-propionylbenzothiazol-2-one is described in Ucar, et al., "Fries-Like' Rearrangement: a Novel and Efficient Method for the Synthesis of 6-Acyl-2(3H)-benzoxazolones and 6-Acyl-2(3H)-benzothiazolones," *Tetrahedron*, 54:1763-1771 (1998). Ucar, et al., "Synthesis and Anticonvulsant Activity of 2(3H)-Benzoxaxolone and 2(3H)-benzothiazolone Derivatives," *J. Med. Chem.* 41:1138-1145 (1998) discloses evaluation of 2(3H)-benzothiazolone derivatives for anticonvulsant activity.

SUMMARY OF THE INVENTION

The use of compounds of the general formula I, and compositions including same, delivers skin lightening benefits with potential reduced irritation. The present invention provides a cosmetic composition and method of skin lightening using a composition comprising in addition to a cosmetically acceptable vehicle, about 0.000001 to about 50% of an N-acylbenzothiazolone compound of general formula I:

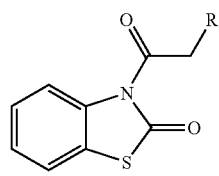

Where R represents a hydrogen atom, $C_1$-$C_4$ acyl group, or $C_1$-$C_4$ alkyl group.

Preferably, R represents a $C_1$ alkyl group, as represented by compound 3-propionylbenzothiazol-2-one of formula II:

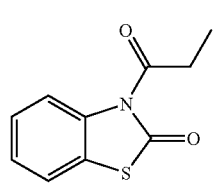

Further skin benefit agents may be included in the inventive cosmetic compositions. Organic and inorganic sunscreens may also be included.

The inventive compounds and compositions may be used for reducing overall skin pigmentation and the reduction of discrete hyperpigmentation, such as blemishes and freckles, as well as for reducing the irritation associated with irritating skin benefit agents, such as retinol.

DETAILED DESCRIPTION OF THE INVENTION

As used herein, the term "cosmetic composition" is intended to describe compositions for topical application to human skin.

The term "skin" as used herein includes the skin on the face, neck, chest, back, arms, axilla, hands, legs, and scalp.

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

It should be noted that in specifying any range of concentration, any particular upper concentration can be associated with any particular lower concentration.

The term "comprising" is used herein in its ordinary meaning and means including, made up of, composed of, consisting and/or consisting essentially of. In other words, the term is defined as not being exhaustive of the steps, components, ingredients, or features to which it refers.

Skin Lightening Agents

The invention is concerned with the use of compounds of general formula I, shown below, and compositions including same, as skin cosmetic agents, particularly as skin lightening agents. A particular advantage of the inventive compositions and methods is that compounds of general formula I can be less irritating to the skin than known skin lightening compounds.

N-acylbenzothiazolone

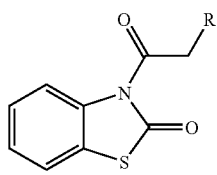

Preferably, R represents a $C_1$ alkyl group, as represented by compound 3-propionylbenzothiazol-2-one of formula II:

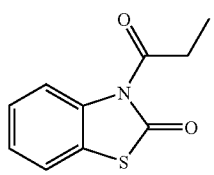

Further skin benefit agents may be included in the inventive cosmetic compositions. Organic and inorganic sunscreens may also be included.

The inventive cosmetic compositions and methods have effective skin lightening properties and may be less irritating to the skin.

The compositions generally contain about 0.000001 to about 50% of compounds of general formula I. Compounds of formula II are preferred. The amount of the compound of general formula I or formula II is preferably in the range of about 0.00001% to about 10%, more preferably about 0.001 to about 7%, most preferably from 0.01 to about 5%, of the total amount of a cosmetic composition.

Optional Skin Benefit Agents

Preferred cosmetic compositions are those suitable for the application to human skin according to the method of the present invention, which optionally, but preferably, include a further skin benefit agent.

Suitable additional skin benefit agents include anti-aging, wrinkle-reducing, skin whitening, anti-acne, and sebum reduction agents. Examples of these include alpha-hydroxy acids, beta-hydroxy acids, polyhydroxy acids, hyaluronic acid, hydroquinone, t-butyl hydroquinone, Vitamin B derivatives, Vitamin C derivatives; allantoin, a placenta extract; dioic acids, retinoids, and resorcinol derivatives.

Cosmetically Acceptable Carrier

The cosmetically acceptable vehicle may act as a dilutant, dispersant or carrier for the skin benefit ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferably oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$-$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

Optional Components

Other adjunct minor components may also be incorporated into the cosmetic compositions. These ingredients may include coloring agents and/or pigments; opacifiers, perfumes, other thickeners, plasticizers; calamine; antioxidants; chelating agents; as well as additional sunscreens, such as organic sunscreens. Amounts of these other adjunct minor components may range anywhere from 0.001% up to 20% by weight of the composition.

Sunscreens

For use as sunscreen, metal oxides may be used alone or in mixture and/or in combination with organic sunscreens. Examples of organic sunscreens include but are not limited those set forth in the table below:

TABLE 1

| CTFA Name | Trade Name | Supplier |
|---|---|---|
| Benzophenone-1 | UVINUL 400 | BASF Chemical Co. |
| Benzophenone-2 | UVINUL D-50 | BASF Chemical Co. |
| Benzophenone-3 | UVINUL M-40 | BASF Chemical Co. |
| Benzophenone-4 | UVINUL MS-40 | BASF Chemical Co. |
| Benzophenone-6 | UVINUL D-49 | BASF Chemical Co. |
| Benzophenone-8 | SPECRA-SORB UV-24 | American Cyanamide |
| Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

The amount of the organic sunscreens in the cosmetic composition is preferably in the range of about 0.1 wt % to about 10 wt %, more preferably about 1 wt % to 5 wt %.

Preferred organic sunscreens are PARSOL MCX and Parsol 1789, due to their effectiveness and commercial availability.

Use of the Composition

The method according to the invention is intended primarily as using a personal care product for topical application to human skin, for cosmetic benefits including but not limited to skin lightening.

The inventive compounds and compositions may be used for reducing overall skin pigmentation and the reduction of discrete hyperpigmentation, such as blemishes and freckles, as well as for reducing the irritation associated with irritating skin benefit agents, such as retinol.

In use, a small quantity of the composition, for example from 1 to 5 ml, is applied to areas of the skin, from a suitable container or applicator and, if necessary, it is then spread over and/or rubbed into the skin using the hand or fingers or a suitable device.

Product Form and Packaging

The cosmetic composition useful for the method of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. When the composition is a solid or semi-solid stick, it may be packaged in a suitable container for manually or mechanically pushing out or extruding the composition.

The invention accordingly also provides a closed container containing a cosmetically acceptable composition as herein defined.

The following examples are by way of example, not by way of limitation, of the principles of the present invention, to illustrate the best mode of carrying out the invention.

EXAMPLE 1

Cosmetic compositions within the scope of the invention were prepared. The 3-propionylbenzothiazol-2-one was synthesized in accordance with the method of Ucar et al., "'Fries-Like' Rearrangement: a Novel and Efficient Method for the Synthesis of 6-Acyl-2(3H)-benzoxazolones and 6-Acyl-2(3H)-benzothiazolones," *Tetrahedron*, 54:1763-1771 (1998), incorporated by reference herein.

A base formulation shown in the Table below was made by heating phase A ingredients to 70 to 85° C. with stirring. Phase B ingredients were heated in a separate container to 70 to 85° C. with stirring. Then, phase A was added into phase B while both phases were kept at 70 to 85° C. The mixture was stirred for at least 15 minutes at 70 to 85° C., then cooled.

TABLE 2

| Ingredients | 2a % wt. | 2b % wt. | Phase |
|---|---|---|---|
| Isostearyl Palmitate | 6.00 | 6.00 | A |
| C12-C15 Alkyl Octanoate | 3.00 | 3.00 | A |
| PEG-100 Stearate | 2.00 | 2.00 | A |
| Glyceryl Hydroxystearate | 1.50 | 1.50 | A |
| Stearyl Alcohol | 1.50 | 1.50 | A |
| Stearic acid | 3.00 | 4.00 | A |
| TEA, 99% | 1.20 | 1.20 | B |
| Dimethicone | 1.00 | 1.00 | A |
| Sorbitan Monostearate | 1.00 | 1.00 | A |
| Magnesium Aluminum Silicate | 0.60 | 0.60 | B |
| Vitamin E acetate | 0.10 | 0.10 | A |
| Cholesterol | 0.50 | 0.50 | A |
| Simethicone | 0.01 | 0.01 | B |
| Xanthan gum | 0.20 | 0.20 | B |
| Hydroxyethylcellulose | 0.50 | 0.50 | B |
| Propylparaben | 0.10 | 0.10 | B |
| Disodium EDTA | 0.05 | 0.05 | B |
| Butylated hydroxytolene | 0.05 | 0.05 | B |
| 3-propionylbenzothiazol-2-one | 0.05 | 2.00 | B |
| Niacinamide | 1.00 | 1.00 | B |
| Metal oxide | 2.50 | 5.00 | B |
| Methylparaben | 0.15 | 0.15 | B |
| Water | BAL* | BAL* | B |
| Total | 100.00 | 100.00 | B |

*BAL means Balance.

EXAMPLE 2

Additional cosmetic compositions within the scope of the invention were prepared.

TABLE 3

| | Wt % | Phase |
|---|---|---|
| water, DI | BALANCE | A |
| disodium EDTA | 0.05 | A |
| magnesium aluminum silicate | 0.6 | A |
| methyl paraben | 0.15 | A |
| simethicone | 0.01 | A |
| butylene glycol 1,3 | 3.0 | A |
| hydroxyethylcellulose | 0.5 | A |
| glycerine, USP | 2.0 | A |
| xanthan gum | 0.2 | A |
| triethanolamine | 1.2 | B |
| stearic acid | 3.0 | B |
| propyl paraben NF | 0.1 | B |
| glyceryl hydroxystearate | 1.5 | B |
| stearyl alcohol | 1.5 | B |
| isostearyl palmitate | 6.0 | B |
| C12-15 alcohols octanoate | 3.0 | B |
| dimethicone | 1.0 | B |
| cholesterol NF | 0.5 | B |
| sorbitan stearate | 1.0 | B |
| Micronized titanium dioxide | 5.0 | C |
| tocopheryl acetate | 0.1 | B |
| PEG-100 stearate | 2.0 | B |
| sodium stearoyl lactylate | 0.5 | B |
| hydroxycaprylic acid | 0.1 | C |
| 3-propionylbenzothiazol-2-one | 10.0 | C |
| PARSOL MCX | 2.4 | C |
| alpha-bisabolol | 0.2 | C |

The composition of this Example was prepared as follows:

1. Heat Phase A to 80° C.
2. Heat Phase B to 75° C. in a separate container
3. Add B to A and mix with heat off for 30 min.
4. At 50° C. add Phase C and mix for 10 min.

EXAMPLES 3-10

A set of additional compositions useful in the methods of the present invention were prepared within the scope of the present invention and are listed in the table below.

TABLE 4

| | | Examples (wt. %) | | | | | | | |
|---|---|---|---|---|---|---|---|---|---|
| Ingredients | Phase | 3 acid soap base | 4 | 5 | 6 | 7 | 8 | 9 | 10 |
| Stearic acid | A | 17.9 | 17.9 | 17.9 | 17.9 | 17.9 | 17.9 | 17.9 | 17.9 |
| Sodium cetearyl sulfate* (emulsifier) | A | | 2.2 | | 1 | 1.5 | 2 | 3 | 2 |
| Myrj 59* (emulsifier) | A | | | 2 | 2 | 2 | 2 | 2 | 1 |

TABLE 4-continued

| | | Examples (wt. %) | | | | | | | |
|---|---|---|---|---|---|---|---|---|---|
| Ingredients | Phase | 3 acid soap base | 4 | 5 | 6 | 7 | 8 | 9 | 10 |
| Span 60* (emulsifiers) | A | | | 2 | 2 | 2 | 2 | 2 | 1 |
| 3-propionylbenzo-thiazol-2-one | B | 0.05 | 0.05 | 2.0 | 2.0 | 3.5 | 3.5 | 5.0 | 10.0 |
| Micronized Zinc Oxide | B | | 2.50 | 5.00 | 5.00 | 2.50 | 2.50 | 5.00 | 2.50 | 5.00 |
| KOH, 22% (form in situ soap with stearic acid) | | 2.20 | | | | | | | |
| Octyl methoxycinnamate | | 2.50 | | | 2.50 | 2.50 | | 2.50 | |
| Water | B | BAL | BAL | BAL | BAL | BAL | BAL | BAL | BAL |
| Glycerin | B | 1 | 1 | 1 | 1 | 1 | 1 | 1 | 1 |

EXAMPLE 11

This example shows the skin lightening effect of using 3-propionylbenzothiazol-2-one as a skin lightening agent in accordance with the inventive method. This experiment was carried out using Melanoderm cultures. Luminescence was measured using a chromameter to assay the degree of melanization of a 3-D skin model.

Method for Melanoderm Cultures

Melanoderm cultures were obtained from MatTek Corporation, Ashland, Mass. The Melanoderm was maintained according to the manufacturer's instructions. The basal media used for the maintenance of the Melanoderm cultures was DMEM supplemented with unspecified quantities of Epidermal growth factor, Insulin, Hydrocortisone, and proprietary epidermal differentiation compounds, in addition to anti-fungal and antibiotics.

For the long term maintenance of the Melanoderms, the basal media was supplemented with both bFGF and a-MSH, compounds which are stimulators of melanocyte growth and melanogenesis. The cultures were fed every other day for a total of 2 weeks—fresh active preparations, prepared in DMSO or culture media, were also applied to the Melanoderms when feeding was performed. Each treatment condition was done in duplicate and digital photographs were taken of the Melanoderm cultures to assess overall pigmentation. As well, microscopic images of the Melanoderms were done to assess the cell viability of the keratinocytes and melanocytes. For further evidence that the treatments were/not cytotoxic, an LDH assay (Promega, Madison, Wis.) was performed on the supernatants from 24 hour post-treatment cultures.

Solvable Melanin Assay

To prepare tissues for assay:

After treatment, tissues are usually frozen until completion of the experiment. Thaw tissues, a few at a time and place in D-PBS to remove excess phenol red from the culture medium and residual test article. Remove a single tissue from the insert. Blot dry and place in 1.7 ml. microfuge tube. Repeat for all samples. Add 250 ul Solvable™ (Tissue and Gel Solubilizer 0.5 M—Packard BioScience Co. Catalogue No. 6NE9100 (NEF910)). Close the tube and make sure that the tissue is completely submerged. Incubate at 60° C. overnight along with standards. In the morning, vortex the samples. Sometimes thick tissues will require additional time to complete the solution process.

To prepare standard:

Dissolve Melanin (Sigma cat. M 8631) in Solvable at 1 mg/ml. The solution may be warmed gently for 15 minutes at 37° C. Store solution in dark.

To prepare standard curve:

Prepare dilutions from the standard containing 0 ug to 250 ug of melanin in a total of 250 ul Solvable. Incubate dilutions along with samples.

To read assay:

Cool samples and standards. Centrifuge at 13,000 rpm for 5 minutes to pellet. Fill microwell plate (C-96) with 200 ul each of samples and standards. There is some foaming of samples when pipetted. Blow gently across the samples to break bubbles prior to reading the plate. Read plate at 490 nM. The results are shown in the table below.

TABLE 5

| | OD = 490 nm |
|---|---|
| mg/ml melanin standard | |
| 800 | 2.727 |
| 400 | 1.321 |
| 200 | 0.573 |
| 100 | 0.321 |
| 50 | 0.184 |
| 25 | 0.065 |
| Controls | |
| DMSO | 1.292 |
| Untreated | 1.259 |
| 3-propionylbenzothiazol-2-one (uM) | |
| 125 | 1.522 |
| 250 | 1.509 |
| 375 | 1.377 |
| 500 | 0.889 |
| 750 | 0.727 |
| 1000 | 0.184 |

From the results tabulated above it appears that 3-propionylbenzothiazol-2-one compounds of the present invention reduce melanin synthesis.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention. Throughout this application, various publications have been cited. The entireties of each of these publications are hereby incorporated by reference herein.

What is claimed is:

1. A cosmetic method of skin lightening comprising applying to the skin a composition comprising:
    a. about 0.000001 to about 50% of a compound of general formula I:
    N-acylbenzothiazolone compound of general formula I:

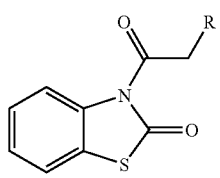

Where R represents a hydrogen atom, $C_1$-$C_4$ acyl group, or $C_1$-$C_4$ alkyl group;
    b. a cosmetically acceptable carrier.

2. The cosmetic method of claim 1, wherein said compound is 3-propionylbenzothiazol-2-one of formula II:

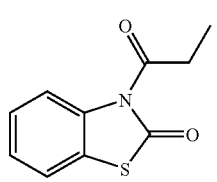

3. The cosmetic method of claim 1, wherein R represents a $C_1$ alkyl group.

4. The method of claim 1, wherein said composition further comprises a sunscreen.

5. The method of claim 2, wherein said sunscreen is a micronized metal oxide.

6. The cosmetic method according to claim 1, wherein said composition further comprises a skin benefit agent selected from the group consisting of alpha-hydroxy acids, beta-hydroxy acids, polyhydroxy acids, betulinic acid, hydroquinone, t-butyl hydroquinone, Vitamin C derivatives, dioic acids, retinoids, resorcinol derivatives, and mixtures thereof.

7. The cosmetic method of claim 1, wherein said composition further comprises an organic sunscreen selected from the group consisting of Benzophenone-3, Benzophenone-4, Benzophenone-8, DEA, Methoxycinnamate, Ethyl dihydroxypropyl-PABA, Glyceryl PABA, Homosalate, Methyl anthranilate, Octocrylene, Octyl dimethyl PABA, Octyl methoxycinnamate (PARSOL MCX), Octyl salicylate, PABA, 2-Phenylbenzimidazole-5-sulphonic acid, TEA salicylate, 3-(4-methylbenzylidene)-camphor, Benzophenone-1, Benzophenone-2, Benzophenone-6, Benzophenone-12, 4-Isopropyl dibenzoyl methane, Butyl methoxy dibenzoyl methane (PARSOL 1789), Etocrylene, and mixtures thereof.

8. A cosmetic composition comprising:
    a. about 0.000001 to about 50% of an N-acylbenzothiazolone compound of general formula I:

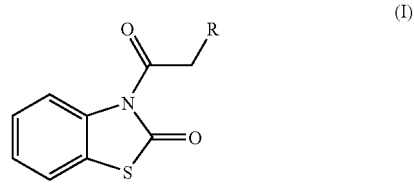

wherein R represents a hydrogen atom, $C_1$-$C_4$ acyl group, or $C_1$-$C_4$ alkyl group; and
    a. a cosmetically acceptable carrier.

9. The cosmetic composition of claim 8, wherein said compound is 3-propionylbenzothiazol-2-one of formula II:

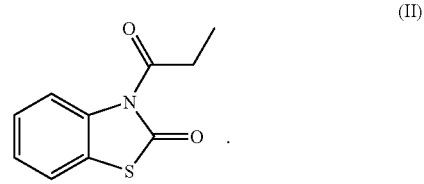

10. The cosmetic composition of claim 9, wherein said compound comprises about 0.00001% to about 10% of said composition.

11. The cosmetic composition of claim 9, wherein said compound comprises about 0.001% to about 7% of said composition.

12. The cosmetic composition of claim 9, wherein said compound comprises about 0.01% to about 5% of said composition.

13. A cosmetic composition for skin lightening, comprising:
    a. about 0.000001 to about 50% of an N-acylbenzothiazolone compound of general formula I:

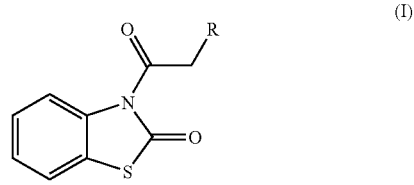

wherein R represents a hydrogen atom, $C_1$-$C_4$ acyl group, or $C_1$-$C_4$ alkyl group; and
    b. a cosmetically acceptable carrier.

* * * * *